(12) United States Patent
Stein et al.

(10) Patent No.: US 12,150,705 B2
(45) Date of Patent: Nov. 26, 2024

(54) DIFFUSING APPARATUS FOR LASER THERAPY TREATMENT

(71) Applicant: Laser Peripherals, LLC, Plymouth, MN (US)

(72) Inventors: Jeffrey M. Stein, Waconia, MN (US); Ricky D. Labrador, Albertville, MN (US); Ratana Vorachack, Champlin, MN (US)

(73) Assignee: Laser Peripherals, LLC, Plymouth, MN (US)

( * ) Notice: Subject to any disclaimer, the term of this patent is extended or adjusted under 35 U.S.C. 154(b) by 445 days.

(21) Appl. No.: 17/630,319

(22) PCT Filed: Nov. 4, 2020

(86) PCT No.: PCT/US2020/058901
§ 371 (c)(1),
(2) Date: Jan. 26, 2022

(87) PCT Pub. No.: WO2021/092024
PCT Pub. Date: May 14, 2021

(65) Prior Publication Data
US 2022/0252776 A1    Aug. 11, 2022

Related U.S. Application Data

(60) Provisional application No. 62/932,879, filed on Nov. 8, 2019.

(51) Int. Cl.
*A61B 18/22* (2006.01)
*F21V 8/00* (2006.01)
(Continued)

(52) U.S. Cl.
CPC ............ *A61B 18/22* (2013.01); *G02B 6/0008* (2013.01); *G02B 6/3624* (2013.01);
(Continued)

(58) Field of Classification Search
CPC ............ A61B 18/22; A61B 2018/2222; A61B 2018/2244; A61B 2018/2261;
(Continued)

(56) References Cited

U.S. PATENT DOCUMENTS 5,219,346 A    6/1993   Wagnieres et al.
5,269,777 A    12/1993  Doiron et al.
(Continued)

FOREIGN PATENT DOCUMENTS

GB      2154761 A       9/1985
WO      2019083920 A1   5/2019

*Primary Examiner* — Scott M. Getzow
(74) *Attorney, Agent, or Firm* — Olson & Cepuritis, Ltd.

(57) ABSTRACT

The present invention provides devices and methods of manufacture related to transmitting light to a target site for diffusion Techniques are provided which allow accurate control of the illumination profile with a diffuser tip design which is easily producible, relatively inexpensive, and provides variations to obtain desired illumination profiles. This is achieved by using at least two light scattering mediums having a shape defined by an insert. The dimensions, light scattering properties, and number of such light scattering mediums may be selected individually or collectively to selectively control the illumination profile. In addition, the insert allows for other beneficial design features, such as a reduced heat retention, easily controlled and refined light scattering medium interfaces, and a smaller cross-sectional diameter than is typically achievable with other techniques. The resulting light transmission and diffusion apparatus is operable with a high efficiency, highly predictable illumination profile, and ease of use.

40 Claims, 12 Drawing Sheets

(51) Int. Cl.
*G02B 6/36* (2006.01)
*A61N 5/06* (2006.01)

(52) U.S. Cl.
CPC ............... *A61B 2018/2222* (2013.01); *A61B 2018/2244* (2013.01); *A61B 2018/2261* (2013.01); *A61B 2018/2272* (2013.01); *A61B 2018/2277* (2013.01); *A61N 5/06* (2013.01); *A61N 2005/063* (2013.01)

(58) Field of Classification Search
CPC .... A61B 2018/2272; A61B 2018/2277; A61B 2018/2266; G02B 6/0008; G02B 6/3624; A61N 5/06; A61N 2005/063
See application file for complete search history.

(56) References Cited

U.S. PATENT DOCUMENTS

| | | |
|---|---|---|
| 2002/0186921 A1 | 12/2002 | Schumacher et al. |
| 2005/0165462 A1 | 7/2005 | Bays et al. |
| 2011/0238139 A1 | 9/2011 | Gowda et al. |
| 2016/0054525 A1 | 2/2016 | Zerfas et al. |
| 2016/0216449 A1* | 7/2016 | Zerfas ................ G02B 23/2423 |
| 2019/0000549 A1* | 1/2019 | Griffin .................. A61B 18/22 |

* cited by examiner

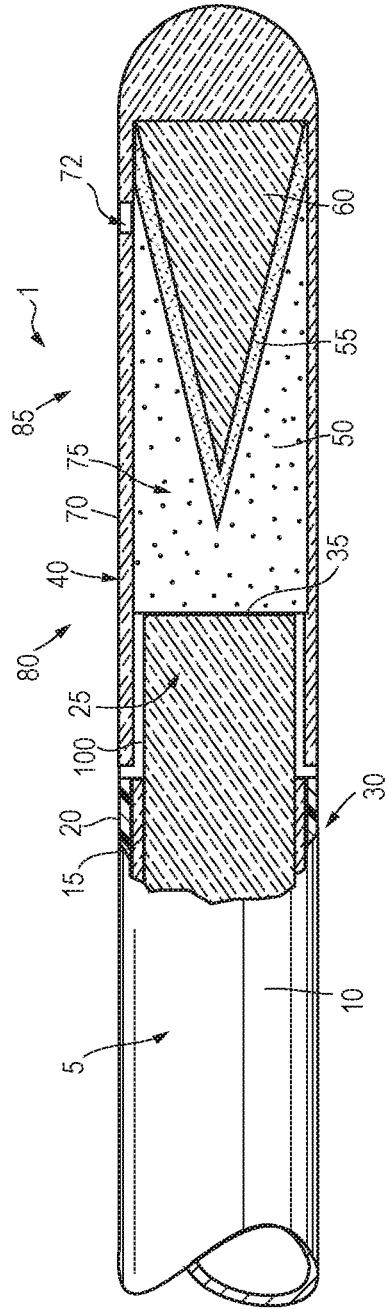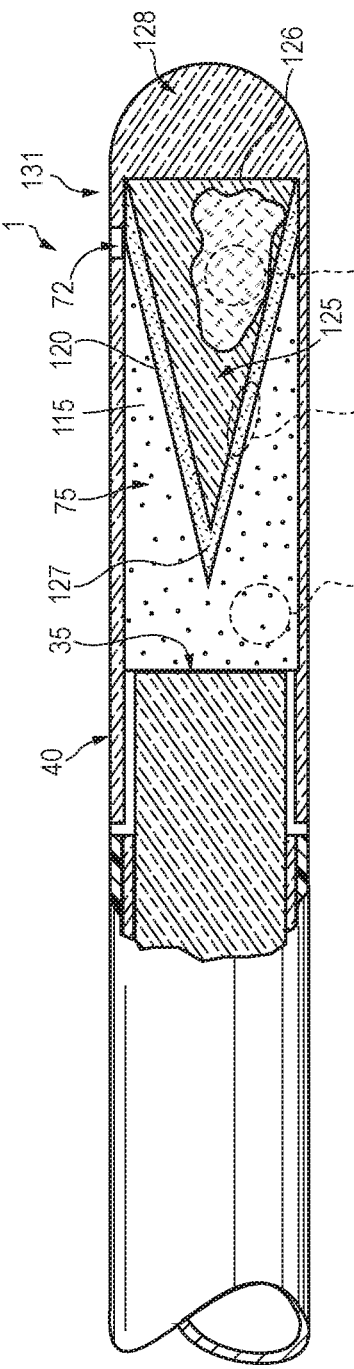

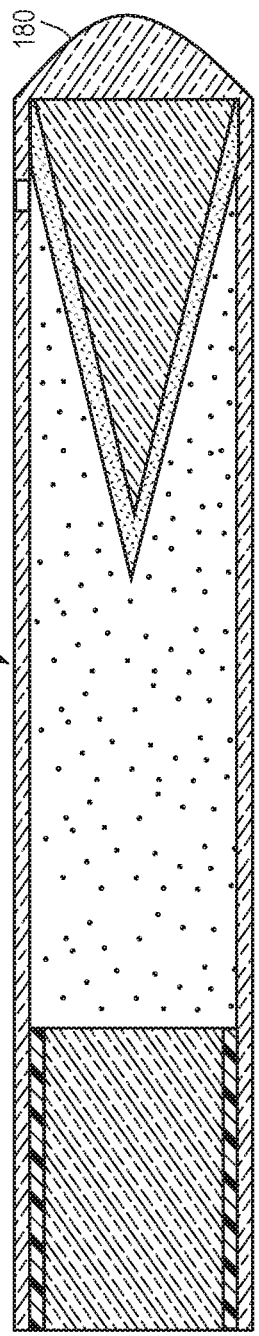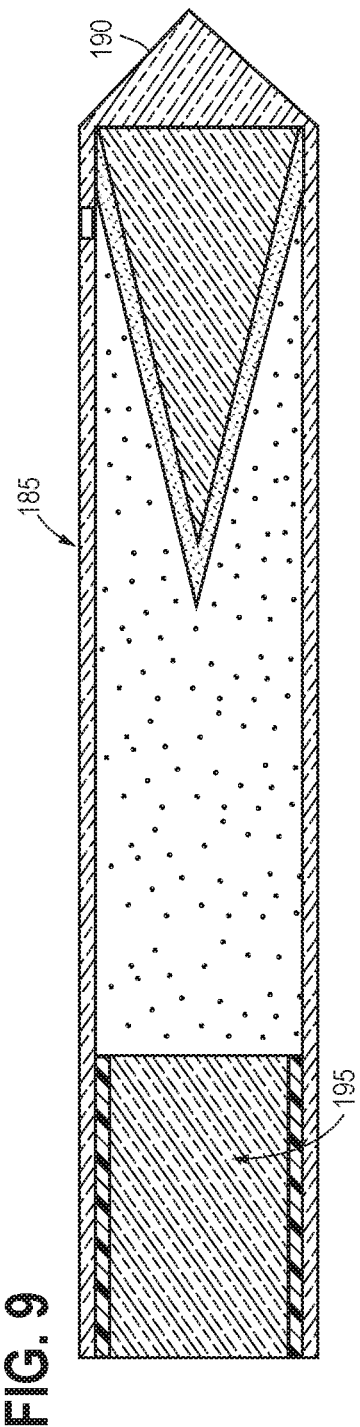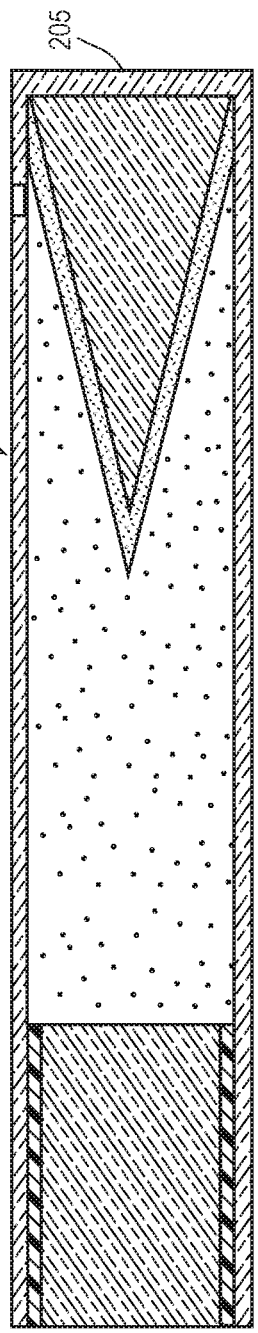

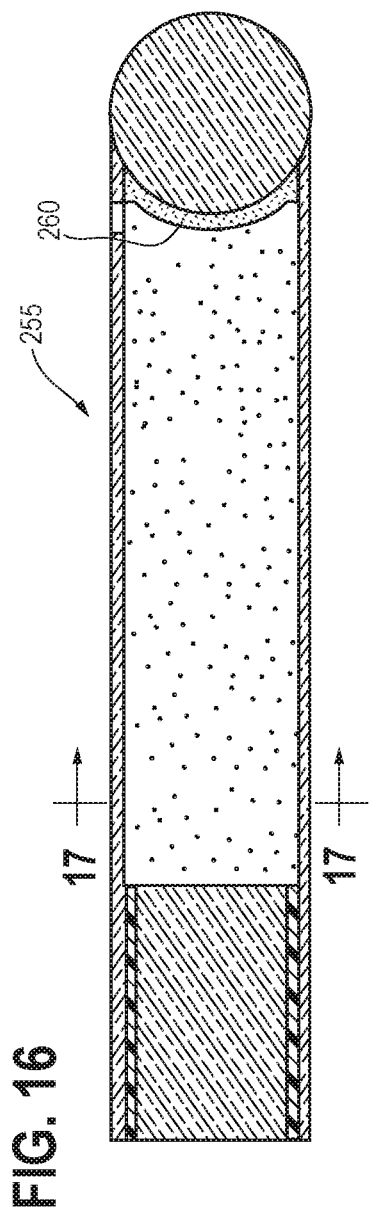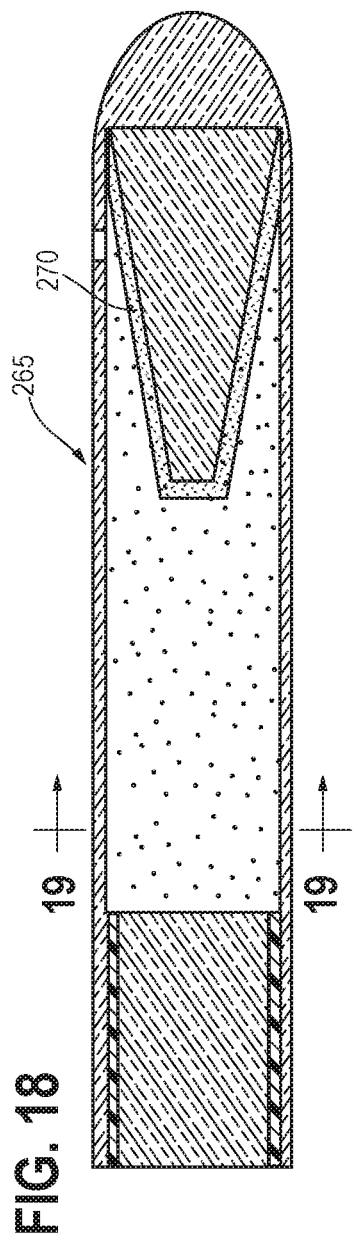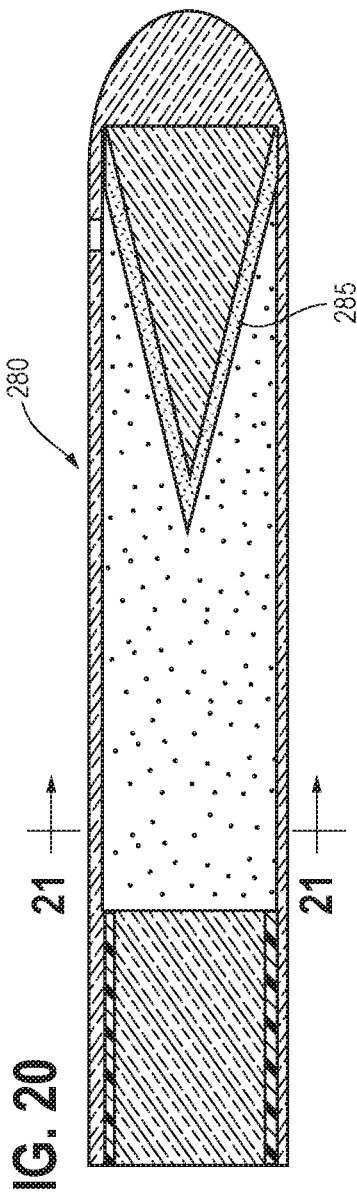

DIFFUSING APPARATUS FOR LASER THERAPY TREATMENT

CROSS-REFERENCE TO RELATED APPLICATIONS

This application is a U.S. National Stage of PCT/US2020/058901, filed Nov. 4, 2020, and claims the benefit of U.S. Provisional Application No. 62/932,879, filed Nov. 8, 2019, which is incorporated herein by reference in its entirety.

FIELD OF THE INVENTION

The invention relates to a light diffusing tip useful in a variety of surgical and therapeutic procedures for clinical applications.

BACKGROUND OF INVENTION

Electromagnetic energy, for example laser energy (light) or guided radiation, is used in a variety of surgical and therapeutic procedures for clinical applications. Such laser systems are often used for transmitting and diffusing light for delivery to a target site to be treated by exposure to the energy. Laser Interstitial Thermal Therapy (LITT), Photodynamic Therapy (PDT), and Photobiomodulation Therapy (PBMT) are examples of clinical tools that use light for treating various medical conditions such as tumors, adenomas, polyps, lesions, infections, swelling, and pain. These methods of clinical treatment utilizing light are often associated with less invasive treatment options, faster recovery times, and a reduced necessity for the extended use of narcotic medications, when compared to conventional surgical procedures.

In LITT, the light emitting end of a light guide is inserted into tissue such as a tumor or adenoma or similar tissue mass, to deliver light within the desired region of treatment. The targeted tissue is then irradiated causing volumetric heating that leads to thermal tissue necrosis. Tumor destruction with direct heating is therefore possible while limiting the side effects and damage to surrounding tissue.

PDT requires that a tissue under treatment be infused with a chromophore having a photoactivated medicinal composition. The tissue is then irradiated with the triggering specific wavelength of light, typically a laser beam delivered by a light guide. When photoactivated medicines are exposed to light, they produce an active form of oxygen that shrinks or destroys nearby cells. The chromophore based medications are metabolized more efficiently by normal tissue, while building up in abnormal tissue such as tumors, as a result, damage to healthy tissue surrounding the abnormal tissue is minimal.

PBMT has been used in the medical community for years. It is generally a treatment in which the energy levels are maintained below the thermal damage threshold of the targeted tissue. Light energy or photons penetrate the tissue, absorbing in naturally occurring chromophores present in living cells. The light energy absorbed by the cell initiates photophysical and photochemical reactions within the cell and adjacent cells. The reaction occurs at the tissue, molecular, and cellular levels within the body and has been shown to result in physiological changes and reactions that result in a therapeutic effect. The effects can range from reducing inflammation and pain symptoms, stimulating the immune system, increased circulation, and enhanced healing of damaged tissue or wounds.

A number of products have been developed to produce a controlled and generally uniform profile of light emitted by a light guide. In one approach, a light emitting section of a light guide is formed by removing a coating or cladding layer covering a core layer and selectively removing sections of the fiber core. This increases the surface area of exposed core at the distal end of the light guide, resulting in the distribution of light emitted from the desired light emitting section of the core.

Other products diffuse light through an optically clear medium a diffusing tip attached to the distal end of the light guide. Some diffusing tips are forward firing, such that the light exits the distal end of the diffusing tip propagating directly forward of the optical axis. In other applications it is necessary to change the direction and distribution of the light emitted by the light guide. To do this, scattering particles may be embedded throughout the diffusing tip. In these products, most of the light is scattered through the diffusing tip immediately adjacent the light emitting section of the light guide. This results in uneven distribution of light along the length and width of the diffusing tip. To improve light distribution, some products have a mirror or other reflective element at the distal end of the diffusing tip to reflect light which has not been sufficiently diffused during its first pass through the diffusing tip. However, this prevents light from being diffused out the distal end and the reflective element can absorb energy creating a hot spot that may char or vaporize adjacent tissue.

In another approach, the diffusing tip utilizes a light scattering medium having continuously increasing light scattering power in a direction parallel to the central axis of the tip. The increased light scattering power is obtained by continuous variation of the concentration of scattering particles embedded in the core medium along the length of the tip. The problem with this diffusing tip design is the difficulty of maintaining uniformity between the layers and providing smooth transitions between the different concentrations of light scattering particles. Another problem is that the increasing concentration of light scattering particles results in increasing amounts of heat retention in the outer layers of the diffusing tip.

To overcome difficulties associated with circumferential scattering, discontinuous sections of scattering medium have been used along the length of the tip, each section having an increased scattering power. With this design, uniform scattering power is still not achieved because there are no smooth transitions between scattering mediums and the sections may have uneven interface angles preventing uniform distribution, resulting in areas of more or less intensity. As light is scattered outwardly of the diffusing tip, the light energy remaining in the fiber decreases. This decreased energy means that less light is available to be scattered at the distal end of the diffusing tip. Also, this design does not resolve the problem of increased heat retention in sections having higher concentrations of light scattering particles.

Although products containing a light scattering medium typically produce more robust and highly flexible diffusing tips, a number of difficulties arise with these approaches. First, uniform light distribution is difficult to achieve with these current designs. Indeed, light emitted near the junction of the fiberoptic tip and diffuser section is substantially more intense than light emitted at the distal end of the diffusing tip. Second, the illumination profile may only be controlled by the consistency of the scattering medium. This prevents the illumination profile from being uniform across the operative length and diameter of the diffusing tip. Third, preparing and manufacturing diffusing tips to provide controlled light diffusing properties is often difficult to achieve, particularly in small diameter diffusing tips having multiple sections of scattering mediums.

Diffusing tips with poor thermal properties may cause trauma to healthy tissue when treating the tumorous volume or other targeted tissue. For example, uneven light distribution can result in localized areas of increased irradiation and heat generation, causing these areas to char and potentially vaporize. As charred tissue continues to absorb energy, its temperature continues to rise, leading to carbonization of tissue around the tip. Further, coagulation of deeper tissue layers is dependent on heat conduction away from this carbonized volume. Alternatively, the consequences of an insufficient heating of the tumor could include incomplete death of the tumor. Incomplete tumor death will result in recurrence of multiple small tumors in the treated area. As such, a diffusing tip that controls and evenly disperses light propagating along the diffusing tip without localized areas of heat retention is desirable.

It is desirable to provide a light diffusion apparatus which overcomes such shortcomings. In particular, it is desirable to provide an apparatus having a diffusing tip which delivers a desired illumination profile through a design which is easily achievable, manufacturable, and controllable. In addition, such designs should be adaptable to various thermal parameters, including, controlled distribution or elimination of heat along the operative length and diameter of the diffusing tip. It is also desirable to provide such a diffusing tip design which is easily adapted to provide other desired illumination profiles and different shaped thermal zones, such as cylindrical, spherical, or elliptical light patterns. Further, it is desirable to provide methods of manufacture related to such an apparatus.

SUMMARY OF INVENTION

An apparatus and methods of manufacture related to transmitting and diffusing electromagnetic energy, for example light for delivery to a target site, are disclosed. It should be understood that the apparatus could be adapted to guide and control the dispersion of a broad range of radiation along the electromagnetic spectrum. However, most medical procedures using a fiber optic delivery system utilize light radiation (wavelengths between about 500 nm and 2200 nm) and therefore the apparatus discussed herein will be discussed in terms of light for efficiency, though it should be understood that the apparatus may be adapted for use with lesser or greater wavelengths of electromagnetic energy depending on the desired application. Specifically, the improved apparatus diffuses light emitted from a light guide in such a manner as to approximate the desired light pattern, including cylindrical, spherical, or elliptical. The apparatus achieves accurate control of the diffused light with an improved diffusing tip design which is easily producible by mass production techniques, inexpensive, and provides substantially uniform illumination profiles. Further, the apparatus is preferably designed to act as its own heat sink, wherein heat retained by light scattering particles is dissipated by sections of glass and sections having lower concentrations of light scattering particles.

The diffusing tip can deliver radiation at power levels in the range of one to two-hundred Watts, or more. This allows a clinician to perform clinical therapy rapidly and uniformly to a large volume of tissue. The diffusing tip may be used as a stand-alone surgical instrument, or when appropriate it may be fixed, either temporarily or permanently, on or within ancillary instruments such as endoscopes, disposable endoscopes, catheters, steerable catheters, imaging and viewing systems, hand pieces, optical systems, reflectors, and liquid or gas cooling systems. It is possible to use the diffusing tip to deliver higher Wattages of radiation, however, an ancillary cooling device may be employed to reduce damage to the light guide and diffusing tip. A cooling device capable of such operation is illustrated by Gowda et al. in U.S. Pat. No. 7,270,656, the disclosure of which is incorporated herein by reference.

The diffusing tip preferably comprises at least two mediums having different refracting characteristics. These mediums and their light scattering properties provide improved light diffusion while maintaining high optical energy radiation values without suffering critical optical, thermal, or mechanical damage. The shapes of the mediums can allow for beneficial design features, such as uniform light distribution profiles across the entire operative length and diameter of the diffusing tip and reduced heat retention. The shape and dimensions of the mediums and the light scattering properties of each medium, among other features, may be selected individually or collectively to selectively control the resulting illumination profile and thermal properties.

In one embodiment, the mediums are preferably a filling, a coating, and an insert. As light propagates through the diffusing tip it enters the first medium, the filling, where the light is scattered by light scattering particles in the filling. Each time the light encounters a scattering particle in the filling, it is deflected. Some of the deflected light exceeds the critical angle for internal reflection and exits the diffusing tip. The remaining light propagates through the diffusing tip to the second medium, the coating, where the light is further deflected by the coating's light scattering particles. Light which is not emitted after deflecting off scattering particles in either the filling or coating hits the insert, the third medium. The outer surface of the insert may have micro-abrasions that further deflect the light, but does not have the heat retention properties of the light scattering particles. Again, if light deflected off the outer surface exceeds the critical angle, it exits the diffusing tip. In another embodiment, the angle and surface quality of the insert may be configured to a critical angle that reflects the forward traveling light outward towards the desired treatment zone. Light which is not deflected by the surface of the insert propagates through the insert and may be diffused through the base and cap at the distal end of the diffusing tip.

In one embodiment, a diffusing tip assembly includes a light guide (e.g. optical fiber), having a core, a cladding, and a buffer, that is connected to a light source. The diffusing tip assembly includes an outer housing alignable with, and adapted to receive, the core of the light guide and serve as a diffuser for light propagating through the light guide. The outer housing preferably comprises three mediums, a filling and a coating—each having different light scattering properties and an insert. Light scattering particles are disposed within the filling and coating. The insert is preferably a transparent material, such as glass, and the outer surface of the insert may have micro-abrasions that diffuse light. Light propagating through the light guide enters the outer housing and a portion of the light is diffused radially outward by the filling, coating, and insert, and another portion of the light is diffused through the distal end of the diffusing tip.

The light diffusing tip can be modified to include optional features. For example, a reflective element can be placed at the distal end of the diffusing tip. In this design, light is not emitted through the distal end, but is retransmitted through the insert, coating, and filling. Alternatively, a light blocking element can be placed at the distal end of the diffusing tip to absorb energy. These embodiments provide selective control of the effected target tissue and thermal zones.

The desired illumination profile may be achieved by altering the shape, size, arrangement, orientation, choice of light scattering particles, concentration of light scattering particles, and other variables related to the filling, coating, and insert within the diffusing tip. Indeed, the amount of light scattering particles and the length of the insert can be controlled such the diffusion of the light along the length and the diameter of diffusing tip is preferably rendered substantially uniform. The term "substantially uniform" is used to describe a light diffuser that possess a degree of uniformity of emitted light of approximately 90 percent of the average intensity of light emitted from a diffusing tip assembly along its operative length, radially, axially, or both. In other applications, it may be desirable to change the illumination profile. To achieve the desired profile, it is possible to manipulate the radial and axial dispersion of light by changing the shape or orientation of the insert.

According to the methods of manufacturing one embodiment, the light diffusing tip can be produced by a number of steps. A length of an outer housing (e.g. a capillary) is formed such that the outer housing has a proximal end, a distal end, and defines a cavity extending the length of the outer housing from the proximal end to the distal end. A purge hole can be formed through a wall of the outer housing adjacent the distal end. An insert is formed such that the insert may have a conical shape with an outer surface and a base. A filling having a first light scattering coefficient is prepared, for example, by mixing a first amount of light scattering particles in a base material. A coating having a second light scattering coefficient also is prepared by, for example, mixing a second amount of light scattering particles in the same or different base material. Then the outer surface of the insert is covered with the coating. The filling is deposited into the cavity at the proximal end until the filling is discharged from the purge hole. Then the insert covered with the coating is inserted into the cavity of the outer housing at the distal end. Then an exposed core of a light guide is inserted into the cavity at the proximal end. When inserting exposed core into the cavity, the filling is pushed through the outer housing and discharged from the purge hole. This discharged filling is removed, the hole is sealed, and the diffusing tip is cured. The steps of this method may be performed in any of various orders.

BRIEF DESCRIPTION OF THE DRAWINGS

FIG. 1 is a schematic diagram illustrating an exemplary light diffusing tip assembly in accordance with at least one embodiment;

FIG. 2 is a schematic diagram illustrating an exemplary light diffusing tip in accordance with at least one embodiment;

FIG. 8 is a schematic diagram illustrating a light diffusing tip having a rounded cap in accordance with at least one embodiment;

FIG. 9 is a schematic diagram illustrating a light diffusing tip having a pointed cap in accordance with at least one embodiment;

FIG. 10 is a schematic diagram illustrating a light diffusing tip having a blunt cap in accordance with at least one embodiment;

FIG. 16 is a schematic diagram illustrating a light diffusing tip having a spherical shaped insert in accordance with at least one embodiment;

FIG. 18 is a schematic diagram illustrating a light diffusing tip having a chisel-shaped insert in accordance with at least one embodiment;

FIG. 20 is a schematic diagram illustrating a light diffusing tip having an angled insert in accordance with at least one embodiment;

DETAILED DESCRIPTION

Figure 2A:
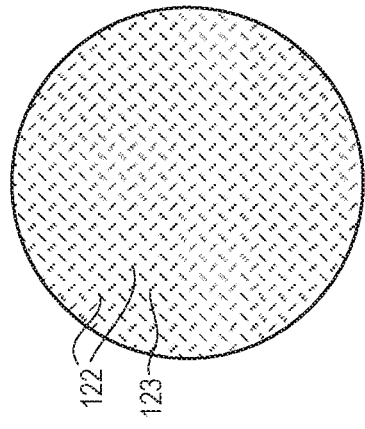
FIG. 2A is a close-up view of an embodiment of a filling base material and light scattering particles in a filling.
Figure 2B:
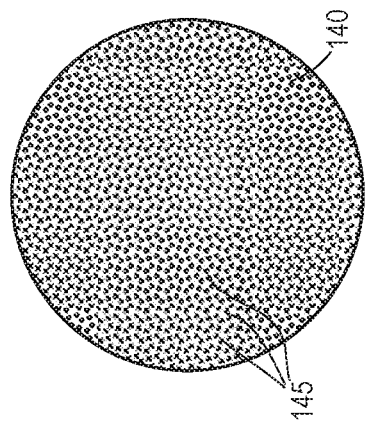
FIG. 2B is a close-up view of an embodiment of a coating base material and light scattering particles in a coating.
Figure 2C:
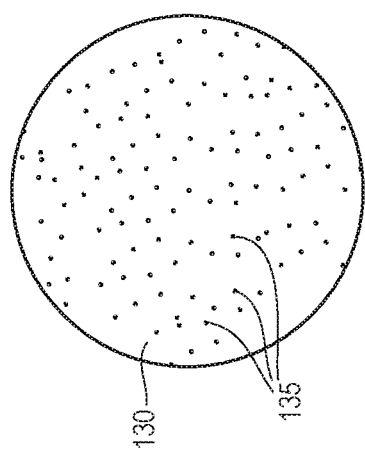
FIG. 2C is a close up view of an embodiment of an insert having micro abrasions on the outer surface.

The detailed description set forth below in connection with the drawings is intended as a description of the particular embodiments and is not intended to represent the only forms in which the present invention may be constructed or utilized. The description sets forth the invention and the sequence of steps for constructing the invention in connection with the illustrated embodiments. It is to be understood, however, that the same or equivalent functions and sequences may be accomplished by different light diffusing tip embodiments that are also intended to be encompassed within the spirit and scope of the invention. Throughout the specification, wherever practicable, like structures will be identified by like reference numbers.

Referring now to FIG. 1, an embodiment of a diffusing tip 1 is shown with a light guide 5 having an optical fiber core 10 surrounded by at least one cladding 15 and a buffer 20. The core 10 may be made of glass, silica, silicon, silicone, quartz, plastic, polymer or fluoropolymer. The core 10 diameter is generally between 50 µm and 2800 µm, and preferably is about 150 µm-1000 µm with 365 µm being a common example. The cladding 15 has a lower refraction index than the core 10, and may also be made of glass, silica, quartz, plastic, or fluoropolymer. Additional cladding layers may have the same or different refraction indexes, and may also be made of glass, silica, quartz, plastic, or fluoropolymer. The core-to-cladding diameter ratio in this example is around 1:1.2. In a preferred embodiment, an inner cladding layer has a diameter of about 400 µm and an outer cladding layer has a diameter of about 425 µm. The buffer 20 may be made of HYTREL, TEFZEL, nylon, polyimide, silicone, acrylate, or polymers. The buffer 20 diameter is generally between 100 µm and 3000 µm, and in a preferred embodiment the buffer diameter is about 730 µm. In some applications, the cladding may serve as the buffer, or the buffer can act as an additional cladding. The numerical aperture of the light guide 5 may be in the range of 0.20 and 0.48, preferably 0.22. The light guide 5 may also be referred to as an optical fiber or fiber optic.

In preparation, a portion of the distal end 30 of the light guide 5 is stripped of its cladding 15 and buffer 20, thereby exposing the core 10 of the light guide 5. In alternative preparations it may also be necessary to strip the light guide 5 of a coating (not shown), or secondary cladding (not shown). The exposed core 25 is preferably cleaved or polished to a flat surface perpendicular to the axis of the core 10. In this embodiment, the perpendicular surface is the light emitting portion 35 of the light guide. Other core termination configurations, such as termination in a point, sphere, or angle, may be implemented as appropriate.

The outer housing 40 of the diffusing tip 1 can be attached to the exposed core 25. The outer housing 40 has a wall 70 that is preferably uniform in thickness thereby providing an axially extending cavity 75 of circular cross-section along the entire length of the outer housing 40. The length of the outer housing 40 is selected based on the intended application of the diffusing tip 1. For example, the outer housing 40 may vary in length from 10 mm to 100 mm depending on the targeted tissue or the desired shape of the thermal zone to be produced around the diffusing tip. As an alternative example, the outer housing 40 may have a length less than 10 mm to minimize the size of the thermal zone. The material used for the outer housing 40 may be flexible or rigid. Preferably, the outer housing 40 may be, for example, a cylindrical tube, hollow waveguide, or a capillary, and is composed of any of a variety of light transmissive materials, such as, for example, polycarbonate, polyurethane, polyethylene, polypropylene, silicon, silica, fused silica TEFLON, polymer, polyimide, sapphire, or quartz. The refractive index of the outer housing 40 may be different than the refractive index of the core 10, 25, cladding 15, or buffer 20. The outer housing 40 generally has an outer diameter that may vary between 100 µm and 3000 µm. Other applications may call for an outer housing having a different shape, including, for example, an outer housing having a triangular, square, rectangular, or oval cross-section.

An adhesive 100 may be used to bond the outer housing 40 to the buffer 20, the cladding 15, the exposed core 25, or any combination of light guide 5 elements. The adhesive 100 may be any high strength, low or high viscosity, 2 part epoxy based, UV curable, or any other optical type adhesive system. For example, an optically transparent epoxy—available from Epoxy Technology, Inc., Billerica, MA, branded as EPO-TEK 301-2 Optically Transparent Epoxy—is a suitable adhesive.

The cavity 75 can have a first portion 80 adapted to receive the core 25 and light emitting portion 35 of a light guide 5 and a second portion 85 adapted to receive light diffusing mediums 50, 55, and a preferably optically clear insert 60. The first portion 80 of the cavity 75 encloses a length of the exposed core 25 such that the outer housing 40 preferably abuts both the buffer 20 and cladding 15. A purge hole 72 through the wall 70 to the second portion 85 of the cavity 75 can allow gas and pressure to escape the cavity when the light diffusing mediums 50, 55 and insert 60 are placed in the cavity. Preferably, the light diffusing mediums 50, 55 and the insert 60 substantially fill the cavity 75 so as to displace gas in the cavity 75. The light diffusing mediums 50, 55 can be a filling 115 and a coating 120. The cavity 75 of the outer housing 40 generally has a diameter that may vary between 50 µm and 2800 µm, and preferably is about 365 µm. The proximal end of the outer housing 40 may have other shapes depending on the interface with the light guide 5.

Referring now to FIGS. 2, 2A, 2B, and 2C, the filling 115, the coating 120, and the insert 125 are shown within the cavity 75 of the outer housing 40. The filling 115 and coating 120 each has a different concentration of light scattering particles 135, 145, preferably ranging to approximately 0.30% particles. The insert 125 preferably has no light scattering particles inside. The filling 115 is made of a base material 130 in which a first amount of light scattering particles 135 can be imbedded. The filling 115 is generally between 0.0025% and 0.0050% scattering particles, and in a preferred embodiment the filling is about 0.0037% scattering particles. The coating 120 is made of a base material 140 in which a second amount of light scattering particles 145 can be imbedded. The coating 120 is generally between 0.15% and 0.30% scattering particles, and in a preferred embodiment the filling is about 0.24% scattering particles.

Different scattering properties between the filling 115 and the coating 120 may be implemented by, for example, using differing quantities of the same type of light scattering particles 135, 145 in each of the base materials 130, 140 such as only titanium oxide or alumina oxide. Different scattering properties can also be achieved by utilizing light scattering particles 135 of one type (e.g., titanium dioxide) in the filling 115 and a light scattering particles 145 of another type (e.g., aluminum oxide) in the coating 120. In a preferred embodiment, the concentration of light scattering particles 135 in the filling 115 is less than the concentration of light scattering particles 145 in the coating 120. As another example, the scattering particles 135, 145 may be of different sizes or shapes so as to exhibit different scattering properties. Indeed, the filling will have a filling refractive index and the coating will have a coating refractive index.

Different scattering properties also may be achieved using base materials 130, 140 with different indexes of refraction. The base material 130 of the filling 115 and the base material 140 of the coating 120 may consist of silica, silicon, silicone, glass, plastic, polymer, optical epoxy, UV curable epoxy, or other transparent material. For example, a medical grade elastomer—available from Dow Corning Corporation, Midland, MI, Product Code 1707680, branded as SILASTIC MDX4-4210 Medical Grade Elastomer with Catalyst—is a suitable base material 130, 140 for the filling 115 and coating 120. To control the light scattering properties of the diffusing tip 1 the base material 130, 140 is preferably free of bubbles. There are a variety of methods available to remove bubbles from the base material 130, 140, including using centrifugal and vibrational forces. It also should be noted that other configurations that include gas bubbles in the base materials 130, 140 or an emulsified liquid also may create other desired light scattering properties, for example a homogenous distribution of micro-bubbles within one or more of the layers.

The light scattering properties of the filling 115 and the coating 120 may be different from each other by a combination of any of scattering particle type, scattering particle size, scattering particle shape, or scattering particle concentration. The light scattering particles 135, 145 may be, for example, titanium oxide, titanium dioxide, alumina oxide, aluminum oxide, powdered diamond, diamond dust, zinc oxide, silver, gold, zirconium oxide, cubic zirconia, zirconia nanoparticles, or any combination thereof. One skilled in the art will appreciate that certain types and sizes of light scattering particles 135, 145 may provide higher scattering power when in the same concentration. In the embodiment shown, the light scattering particles 135, 145 are generally less than 100 nm, preferably less than 50 nm. For example, if aluminum oxide particles are used as the light scattering medium, it is preferable the length of the particles be less than 18 nm. Light scattering particles made of titanium oxide are preferably less than 50 nm. A suitable light scattering particle 135, 145 for the filling 115 and coating 120, for example, is a titanium oxide nanopowder, available from US Research Nanomaterials, Inc., Houston, TX, Stock #US3490, CAS #: 13463-67-7-titanium oxide nanopowder ($TiO_2$, anatase, 99.9%, 18 nm).

In a preferred embodiment, the coating 120 comprises a mixture of 0.008 grams of titanium oxide nanopowder, 3.0 grams of silicone, and 0.3 grams of hardener. The preparation of the preferred filling 115 requires a first step mixing a preliminary composition comprising 30.0 grams of silicone, 3.0 grains of hardener, and 0.008 grams of titanium oxide. Then 6.0 grams of the preliminary composition is mixed with 30 grams of silicone and 3 grams of hardener to create the preferred filling 115.

The insert 125 may have a conical shape that tapers from a base 126 to a point called the apex 127. This conical shape has a circular cross-section where the diameter at the base 126 is preferably the same as the diameter of the exposed core 25, and may vary between 50 µm and 2800 µm. The length of the insert 125 is selected based on the intended application. For example, the insert 125 length may vary from 1 mm to 20 mm where a shorter length will produce a thermal zone having a generally spherical shape, and a longer length will produce a thermal zone having a generally cylindrical shape around the diffusing tip 1. The insert 125 may consist of transparent materials having a refractive index, including glass, silica, silicon, silicone, quartz, plastic, polymer or fluoropolymer, sapphire, plastic, engineered plastic, other transparent materials, or metal. The insert 125 outer surface 123 and base 126 may be smooth, depending on the application and diffusing effect. Alternatively, the outer surface 123 and base 126 may be pitted, scratched, scuffed, engraved, abraded, or preferably etched with micro-abrasions 122 to create another interface that increases the diffusing tip's light scattering properties. The outer surface 123 of the insert 125 may be straight, however, a curved outer surface may be preferable depending on the application.

The insert 125 as shown is preferably is substantially coaxial with the axis of the cavity 75, and the apex 127 faces the light emitting portion 35 of the light guide 5. The insert 125 may be distal to the light emitting portion 35 of the light guide 5 and proximal to the distal end 131 of the diffusing tip 1. The distal end 131 of the diffusing tip may have a cap 128 which may be formed by joining the insert 125 and outer housing 40 by, for example, fusion, bonding, welding, adhesion, or mechanical means. Examples of such joining methods may include the use of a fusion-splicer, arc-plasma electrodes, laser welding system, or UV curing device. As another example, the cap 128 can be formed from separate material and then joined with the insert 125 and outer housing 40. The cap 128 may have any shape, for example, square, round, conical, beveled, flat or pyramidal.

Figure 3:
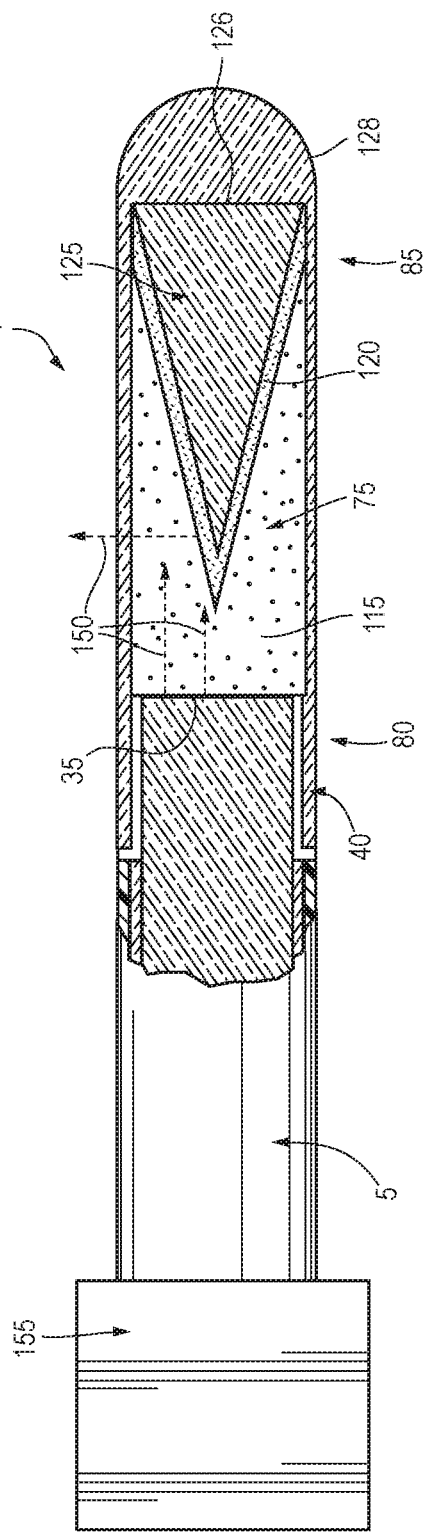
FIG. 3 is a schematic diagram illustrating the diffusion of light rays through one embodiment of the diffusing tip.
Figure 4:
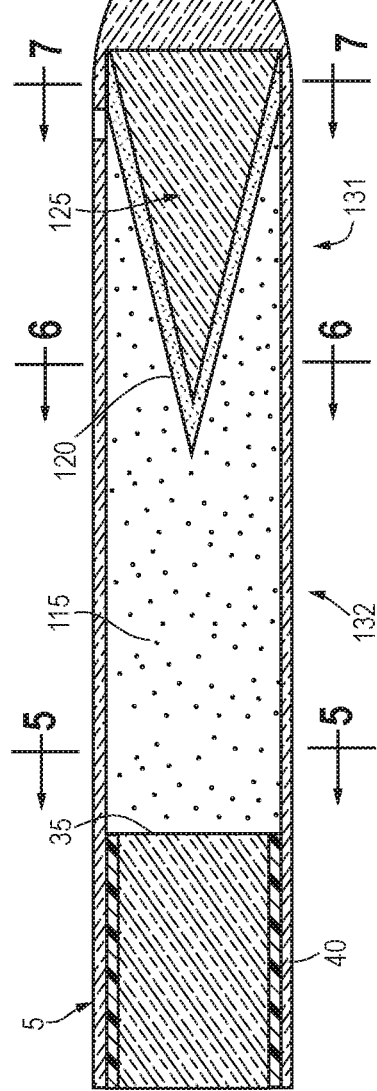
FIG. 4 is a cross-section view illustrating the light diffusing tip in accordance with at least one embodiment.

The diffusion of light rays 150 which can be transmitted from a light source 155, propagated through the light guide 5, and diffused through the diffusing tip 1 is illustrated in FIG. 3. As shown, the outer housing 40 is preferably alignable with, and adapted to receive, the light emitting portion 35 of the light guide 5 and serve as a diffuser for light 150 propagating through the light guide 5. Light 150 propagated by the light guide 5 exits the light emitting portion 35 and is directed into first portion 80 of the cavity 75 of the outer housing 40. Rays 150 traveling axially along the diffusing tip 1 are preferably first scattered by light scattering particles 135 in the filling 115. Each time the light encounters a light scattering particle 135 in the filling 115, the light 150 is deflected until some of the light 150 exceeds the critical angle for internal reflection and exits the outer housing 40. Although scattered rays 150 are illustrated as directed at a right angle to the cavity 75 axis, it should be appreciated that scattered rays 150 are directed in substantially all directions transverse to the cavity axis and through base 126 and cap 128. The remaining light 150 continues to propagate through the diffusing tip 1 to the coating 120. The light 150 that encounters a light scattering particle 145 in the coating 120 is further deflected until some of the light 150 exceeds the critical angle for internal reflection and exits the diffusing tip 1. Rays 150 that reach the light scattering particles 145 in the coating 120 are scattered to a higher degree due to a higher concentration of light scattering particles 145 compared to the concentration of light scattering particles 135 in the filling 115. Light 150 which is not emitted after deflecting off scattering particles 135, 145 in either the filling 115 or coating 120 encounters the outer surface 123 of the insert 125, and again, if the light 150 deflected off the outer surface 123 exceeds the critical angle, it exits the diffusing tip 1. In a preferred embodiment, the conical shape of the outer surface 123 in conjunction with micro-abrasions 122 on the outer surface 123, increases the scattering of rays 150 reaching the distal end of the diffusing tip 1 in a desirably uniform illumination profile. Consequently, some light rays 150 are scattered radially by the conical region 120, 125, other light rays 150 are backscattered toward the light emitting portion 35 of the light guide 5, and the remaining rays 150 continue through the insert 125 and can be diffused through the base 126 and cap 128.

The light is preferably diffused within approximately 90% uniformity along its operative length, axially, or both in this embodiment. However, if the shape of the insert 125 is changed, the radial and axial dispersion of light will also change.

As light 150 is gradually scattered transverse the cavity 75 axis, the light energy remaining in the diffusing tip 1 decreases in intensity. This decreased energy means that less light is available to be scattered. However, as light 150 approaches the distal end 131 of the outer housing 40, the surface area of light scattering particles 135, 145 preferably increases in a controlled manner, the increase being controlled at least in part by the concentration of light scattering particles 135, 145, the shape of the insert 125, and the micro-abrasions 122. Since less light rays 150 enter the insert 125 as compared with rays 150 passing through the filling 115 and the coating 120, the light scattered out of the diffusing tip 1 and the light passing through the base 126 and cap 128 is substantially uniform in intensity over the length and the diameter of the diffusing tip 1. That is, the light emitted 150 along the continuum of the diffusing tip 1 and across the base 126 through the cap 128 remains substantially uniform even though the concentrations of light scattering particles 135, 145 in different areas of cross-sections of the diffusing tip 1 vary. Thus, the conical shape outer surface 123 of the insert 125 results in a highly efficient diffusing tip 1 having a light diffusion profile of approximately 90% uniformity. Indeed, the energy density measured across the base is preferably the same as the energy density measured along the length.

Figure 7:
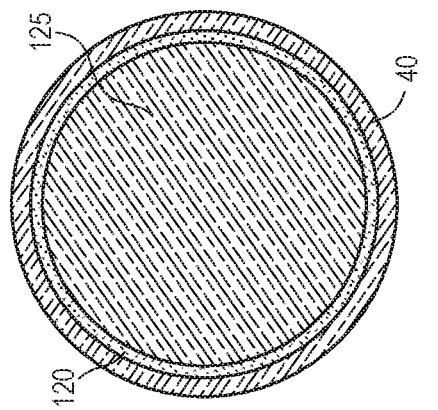
FIG. 7 is a lateral cross section taken through slice 7 as shown in FIG. 4, showing the outer housing, coating, and insert.
Figure 6:
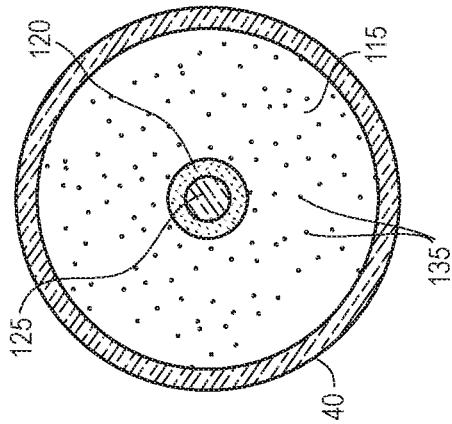
FIG. 6 is a lateral cross section taken through slice 6 as shown in FIG. 4, showing the outer housing, filling, coating, and insert.
Figure 5:
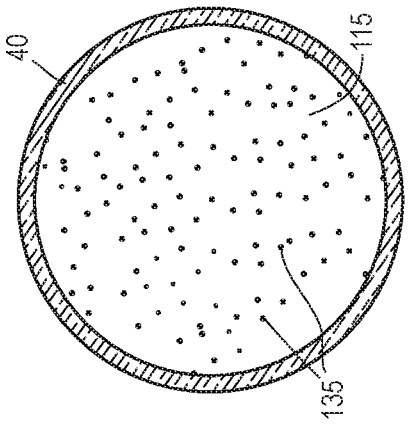
FIG. 5 is a lateral cross section taken through slice 5 as shown in FIG. 4, showing the outer housing, filling base material and light scattering particles in the filling.

FIGS. 4, 5, 6, and 7 depicts cross-sectional views of the diffusing tip 1. The geometric relationship between the filling 115, coating 120, and insert 125 varies along the length of the outer housing 40. As the distance from light emitting portion 35 of the light guide 5 increases, the cross-sectional area of the filling 115 preferably decreases while the cross-sectional areas of the coating 120 and insert 125 increase. As shown in FIG. 5, the diffusing tip 1 is made up of the filling 115 and outer housing 40. As shown in FIG. 6, the surface area of filling 115 preferably decreases and the surface area of the coating 120 and insert 125 increases. As shown in FIG. 7, the diffusing tip 1 is almost entirely made up of the insert 125. Thus, the proportion of the insert 125 to the filling 115 and coating 120 preferably increases from the proximal end 132 to the distal end 131 of the diffusing tip 1. As another example, the concentration of light scattering particles 135 in the filling 115 is preferably lower than the concentration of light scattering particles 145 in the coating 120 and, therefore, the effective concentration of light scattering particles 135, 145 preferably increases over the length of the diffusing tip 1 even as the intensity of the light energy inside the cavity 75 decreases.

Figure 11:
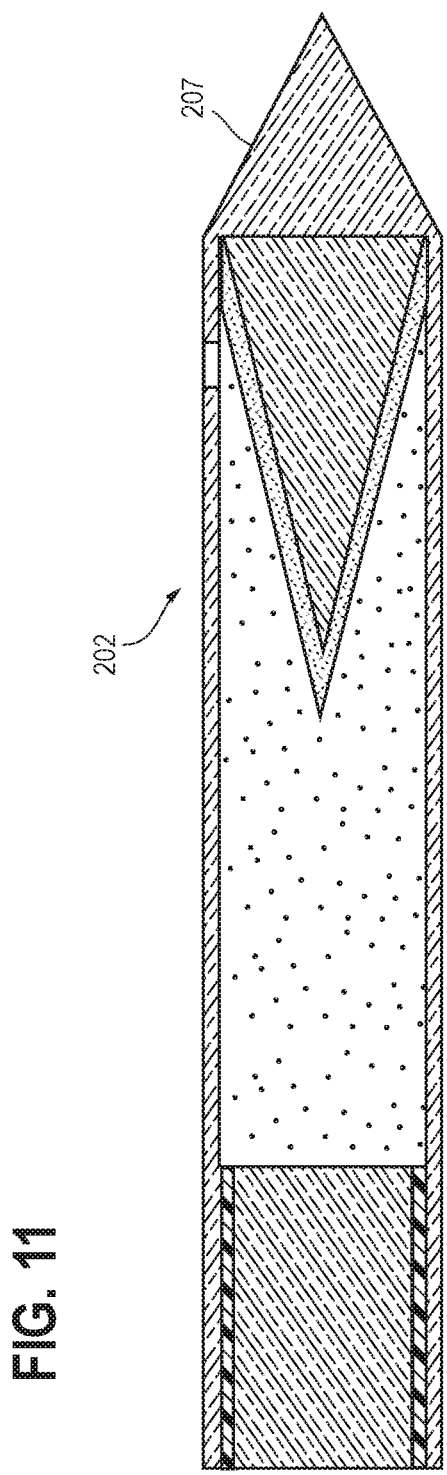
FIG. 11 is a schematic diagram illustrating a light diffusing tip having a chisel-shaped cap in accordance with at least one embodiment.

Referring now to FIGS. 8-11, embodiments of diffusing tips having various shaped caps formed on the distal end of the outer housing are depicted. FIG. 8 depicts a diffusing tip 175 having a rounded cap 180 that may be used in hollow organs with open lumens or to minimize risk of vascular perforations during interstitial applications. FIG. 9 depicts a diffusing tip 185 having a pointed cap 190 that facilitates insertion of the diffusing tip 185 and light guide 195 into tissues for interstitial applications. FIG. 10 depicts a diffusing tip 200 having a blunt cap 205. FIG. 11 depicts a diffusing tip 202 having a chisel shaped cap design 207 that also facilitates insertion of the diffusing tip 202 into tissues for interstitial applications.

Figure 12:
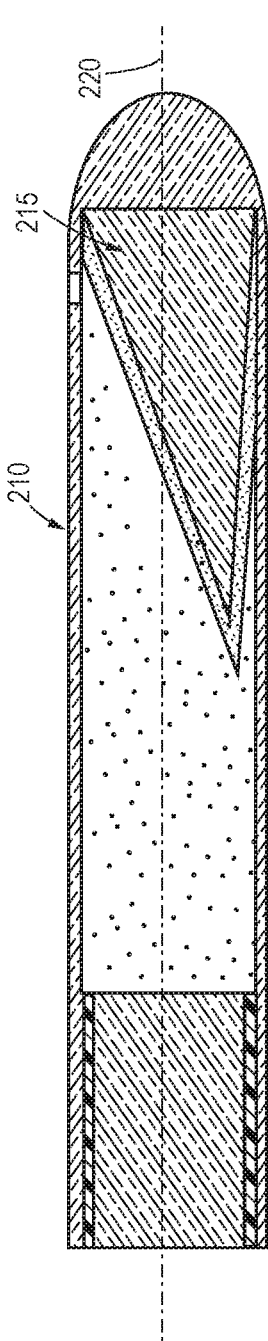
FIG. 12 is a schematic diagram illustrating a light diffusing tip having an insert offset from the cavity axis in accordance with at least one embodiment.
Figure 13:
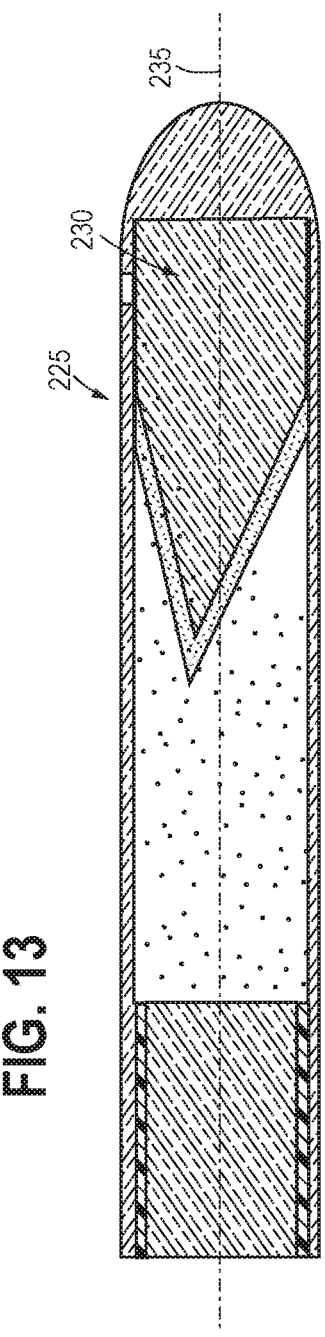
FIG. 13 is a schematic diagram illustrating a light diffusing tip having an insert offset from the cavity axis in accordance with at least one embodiment.
Figure 14:
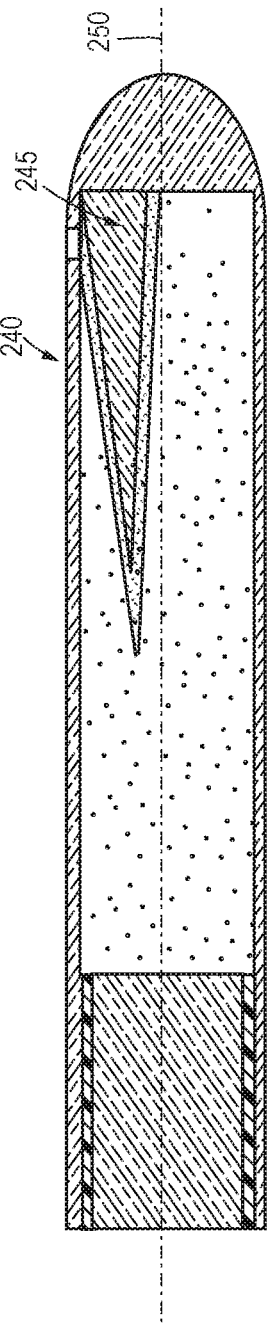
FIG. 14 is a schematic diagram illustrating a light diffusing tip having an insert wholly offset to one side of the cavity axis in accordance with at least one embodiment.
Figure 15:
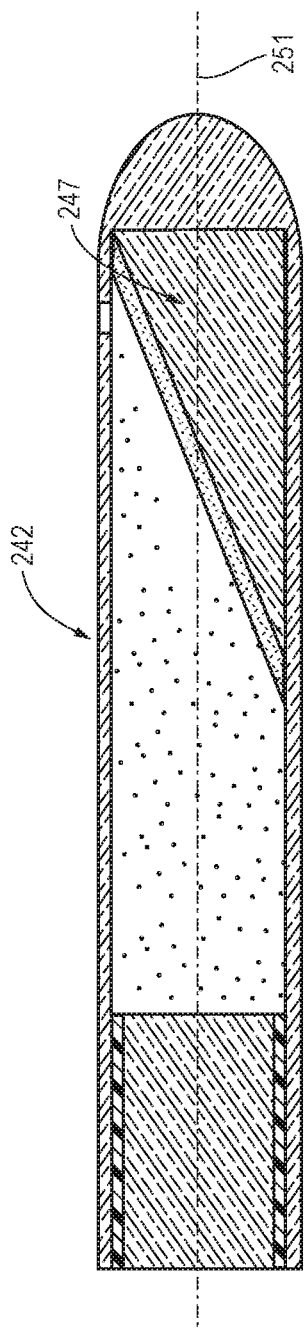
FIG. 15 is a schematic diagram illustrating a light diffusing tip having an insert at an angle to the cavity axis in accordance with at least one embodiment.

FIGS. 12-15 illustrate other embodiments of a diffusing tip having a filling, coating and insert, wherein the insert is offset from the cavity axis. Whereas the exemplary diffusing tips of FIGS. 1-12 are illustrated as having an insert that is substantially coaxial with the cavity axis, the axis of the insert can be offset from the cavity axis as illustrated in FIGS. 12-15. FIG. 12 depicts a diffusing tip 210 having an insert 215 offset from the cavity axis 220. FIG. 13 is another embodiment depicting a diffusing tip 225 having an insert 230 offset from of the cavity axis 235. FIG. 14 depicts a diffusing tip 240 where the insert 245 is wholly offset to one side of the cavity axis 250. FIG. 15 depicts a diffusing tip 242 where the insert 247 is at an angle of between 30 degrees and 60 degrees, preferably a 45 degree angle to the cavity axis 251. The surface of the insert could have any shape however, including convex, concave, rounded, or other contoured surface. Such an implementation may be employed to preferentially diffuse light out of a desired region of the diffusing tip in order to facilitate tissue destruction, avoid damaging healthy tissue, or aid surgical access depending on the location of the target tissue.

Figure 21:
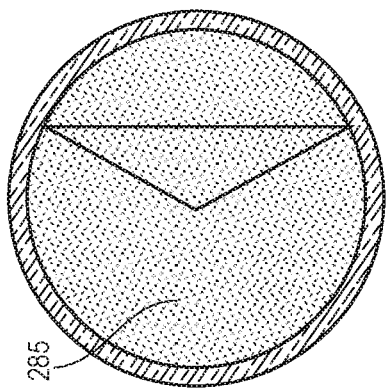
FIG. 21 is a lateral cross section taken through slice 21 as shown in FIG. 19, showing the outer housing and insert.
Figure 19:
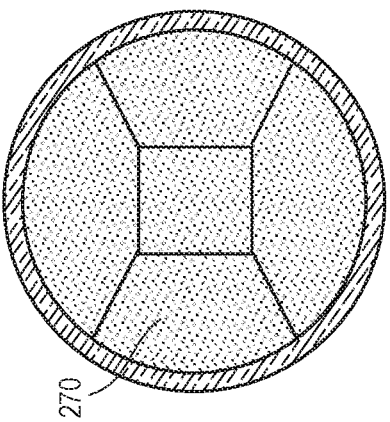
FIG. 19 is a lateral cross section taken through slice 19 as shown in FIG. 18, showing the outer housing and insert.
Figure 17:
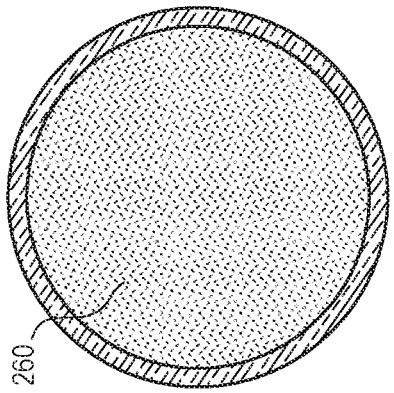
FIG. 17 is a lateral cross section taken through slice 17 as shown in FIG. 16, showing the outer housing and insert.
Figure 22:
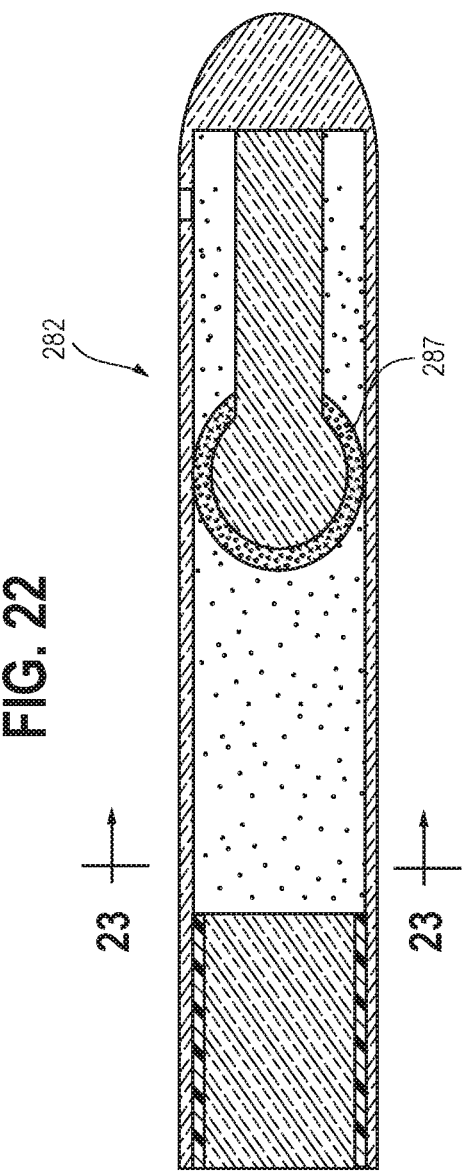
FIG. 22 is a schematic diagram illustrating a light diffusing tip having a spherical shaped insert in accordance with at least one embodiment.
Figure 23:
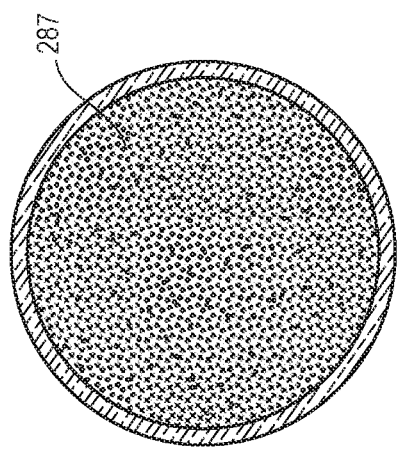
FIG. 23 is a lateral cross section taken through slice 23 as shown in FIG. 22, showing the outer housing and insert.

Depending on the application, other insert shapes are also possible, including spherical, pyramidal, cylindrical, tetrahedron, or asymmetric shapes. Referring now to FIGS. 16-23, embodiments of diffusing tips having various shaped inserts are depicted. FIGS. 16 and 17 depict a diffusing tip 255 having a spherical insert 260. FIGS. 18 and 19 depict a diffusing tip 265 having a chisel-shaped insert 270. FIGS. 20 and 21 depict a diffusing tip 280 having an angled insert 285. FIGS. 22 and 23 depict a diffusing tip 282 having an insert having a spherically-shaped tip 287. In another embodiment, optical coatings such a gold, silver, or dielectric layers may be applied to one or all of the physical components of the diffusing tip to concentrate the diffused light energy in one or more portions along or about the axis of the diffusing tip. As an example, this configuration may be desirable if the target tissue is located only on one side of the esophagus or any other open-lumen body structure.

Figure 24:
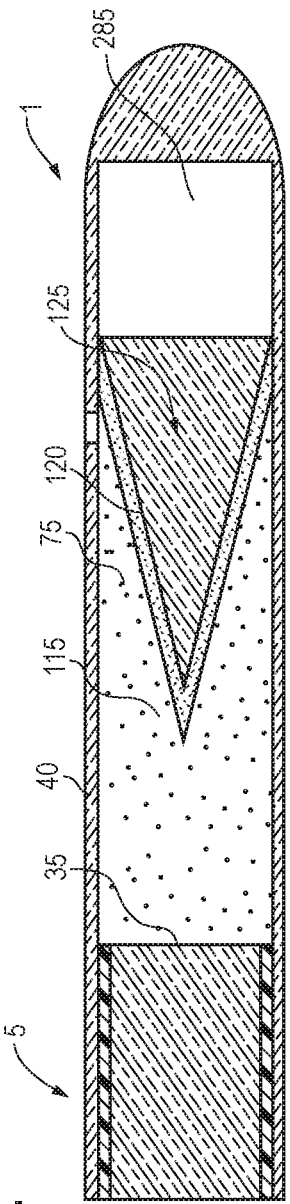
FIG. 24 is a schematic diagram illustrating a light diffusing tip having a light blocking element adjacent the base of the insert in accordance with at least one embodiment.
Figure 25:
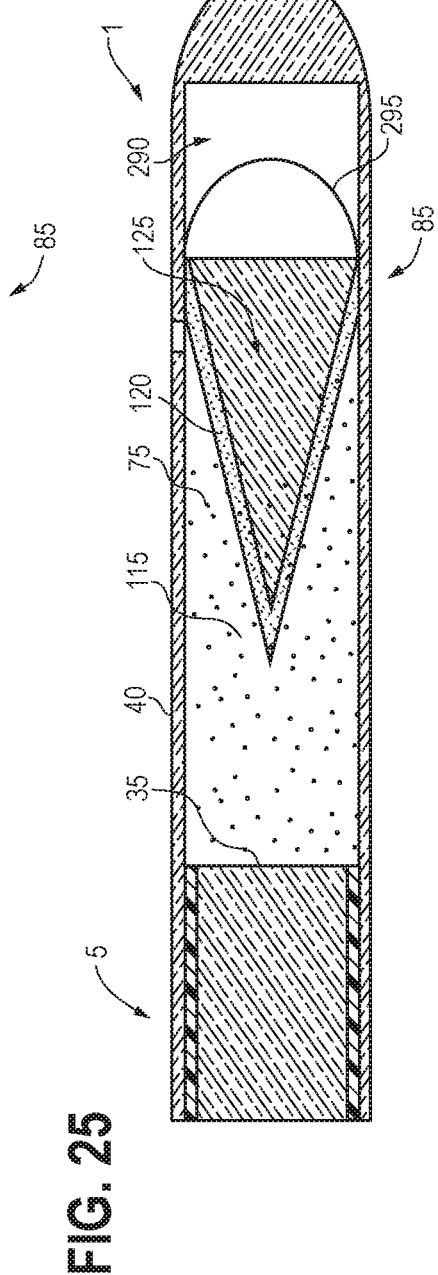
FIG. 25 is a schematic diagram illustrating a light diffusing tip having a concave-shaped light reflecting element adjacent the base of the insert in accordance with at least one embodiment.
Figure 26:
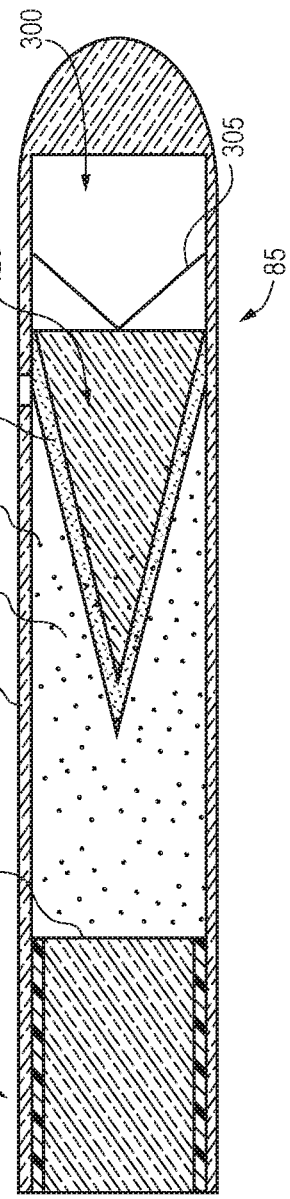
FIG. 26 is a schematic diagram illustrating a light diffusing tip having an angled light reflecting element adjacent the base of the insert in accordance with at least one embodiment.

Referring now to FIGS. 24-26, embodiments of diffusing tips 1 having various light reflecting or light blocking elements are depicted. The reflecting element or light blocking element is preferably disposed in the second portion 85 of the cavity 75 in axial alignment with the light emitting portion 35 of the light guide 5. FIG. 24 depicts a diffusing tip 1 having a light blocking element 285 disposed in the second portion 85 of the cavity 75 of the diffusing tip 1. When a light blocking element 285 is employed, light rays passing through the light guide 5 and exiting the light emitting portion 35 are partially or fully absorbed by the light blocking element 285. The light blocking element can be made of brass, copper, gold, silver, aluminum, titanium, glass, or another metallic or optical material which can be coated or uncoated such that it sufficiently blocks the forward traveling light energy by absorbing, partially reflecting, or a combination of both, for example. In another embodiment, the light blocking element may be an adjustable shroud (not shown) coupled to the diffusing tip and extending a portion of the outer housing. The adjustable shroud substantially prevents the laser light energy from passing through the shroud and into adjacent tissue.

When a reflector is used, the light rays passing through the diffusing tip are reflected by the reflector and returned through the diffusing tip 1. During the second pass, the remaining light rays again encounter the insert 125, coating 120, and filling 115, which provide further circumferential diffusion of the light. The reflecting element can be any reflective material, including, for example, brass, copper, aluminum, titanium, silver, gold, titanium, glass, or another metallic or optical material which can be coated or uncoated such that it sufficiently blocks the forward traveling light energy by reflecting it along an alternate path. FIG. 25 depicts a diffusing tip 1 having a reflecting element 290 having a concave surface 295 adjacent to the insert 125, thereby, varying the light scattering properties of the diffusing tip 1. The reflecting surface of the reflecting element could have any shape, however, including conical, convex, spherical, or flat perpendicular to the cavity axis. In FIG. 26, yet another alternative design for the reflector element 300 is shown, wherein the reflective surface 305 is angled from the cavity axis.

Figure 27:
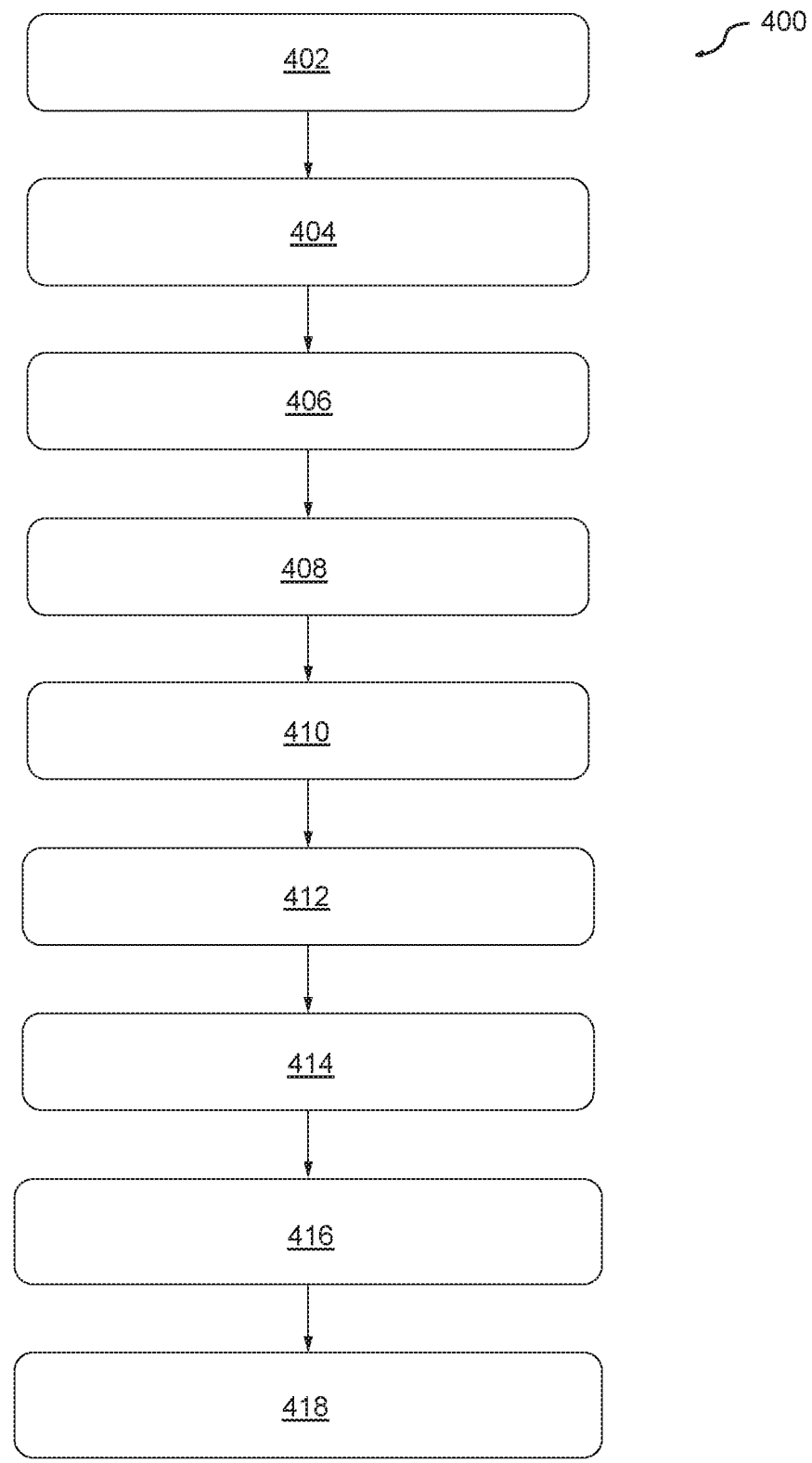
FIG. 27 is a flowchart depicting a manufacturing process of an embodiment of the diffusing tip.

FIG. 27 provides a flowchart 400 directed to the preferred manufacturing process of the light diffusing tip, an example of which is described below in detail. According to the methods of manufacturing an embodiment of the invention, the light diffusing tip is processed by a number of steps. These steps are merely exemplary of the order these steps may occur. The steps may occur in any order that is desired such that it still results in the manufacture of an embodiment of the invention.

Step 402: Form an outer housing having a proximal end, a distal end, and defining a cavity having a cavity axis. Then a purge hole is formed through a wall of the outer housing, approximately one millimeter from the distal end of the outer housing.

Step 404: Form a hole through a wall of the outer housing, approximately one millimeter from the distal end. The hole may be formed using a $CO_2$ laser or using other known methods. After forming the outer housing and the hole, the outer housing is inspected under a microscope for any debris and cleaned by dipping the outer housing in a solvent, preferably methanol.

Step 406: Form an insert, the insert having an outer surface and a base. The insert may comprise any transparent medium having substantially optically clear properties, for example a 365 μm fiber. The 365 μm fiber may be placed on a polishing machine (e.g. an ECOMET 250 grinder polisher) preferably employing 600 grit sandpaper which may grind approximately 8 mm of the outer surface of the fiber into conical shape.

Step 408: Create a filling having a first light scattering coefficient, for example, by mixing a first amount of light scattering particles in a base material.

Step 410: Create a coating having a higher light scattering coefficient than the filling. The coating may be created by, for example, mixing a higher amount of light scattering particles in a base material. To illustrate, the light scattering particle and elastomer mixtures may include, for example, titanium dioxide particles mixed in silicone epoxy. To minimize or eliminate air bubbles in the scattering materials, the filling and coating may be subject to centrifugal force prior to use.

Step 412: Cover the outer surface of the insert with the coating. A coating board is cleaned with methanol and then the coating is placed onto the coating board. The insert is then rolled through the coating to ensure that a thin layer of coating covers the outer surface of the insert. Alternative methods of covering the insert with the coating may be utilized, for example, the coating could be applied to the insert dielectrically. To cure the coating, heat is applied to the coating and insert for approximately thirty seconds. After curing, the insert is cleaned and inspected.

Step 414: Place the coated insert into the cavity of the outer housing at the distal end. Preferably, the apex of the insert is first inserted into the cavity and then the base is aligned flush with the distal end of the outer housing. An alignment tube may be placed into the cavity at the proximal end of the outer housing over the apex of the insert to axially align the apex on the cavity axis. The insert can be inspected to ensure that the apex is centered on the cavity axis.

The distal end of diffusing tip is sealed by placing the outer housing and insert assembly into a capsule holder. Heat is applied to the distal end to fuse the insert and outer housing together and form a cap. The cap may be formed into any shape, for example conical, hemispherical, or flat. After the assembly is cooled, it may be inspected to ensure the base of the insert is completely fused to the outer housing.

Step: 416: Fill the proximal end of the cavity with the filling until the filling is discharged from the hole. An injection tube or any other means suitable for injecting such a medium into the proximal end of the outer housing may be used. For example, the filling is transferred to an injector barrel supplied with a blunt ended needle (e.g., a 27 gauge needle). The needle is introduced into the proximal end of the outer housing and a plunger tip within the barrel is actuated either manually or using a regulated dispenser to inject filling into the cavity of the outer housing. The filling may be injected until, for example, the filling fills the cavity, displacing all the gas, and discharges from the hole at the distal end. At this point, the needle may be removed from the proximal end of the outer housing while continuing to inject.

Step 418: Position the proximal end of the outer housing over the core of a light guide where the cladding and buffer was preferably removed. The outer housing is positioned over a length of the core such that it abuts the cladding and buffer. In one embodiment, the outer housing has an outer diameter selected to substantially match the outer diameter of the light guide's protective jacket so that a uniform surface profile is provided along the entire length of the light guide and diffusing tip. The wall thickness of the outer housing may be selected to allow space for a bonding region between the inner wall of outer housing and the exposed core. The distance between the light emitting end portion and the distal end is typically in the range of approximately 0 mm to 100 mm. The light guide may be a standard optical fiber suitable for transmitting ultraviolet, visible, and near infrared light.

When the core of the light guide or the insert is deposited into the cavity, additional filling is pushed through the outer housing and discharged from the hole. The filling should be checked to see if any foreign matter or air bubbles are visible in the filling. If foreign matter or air bubbles are present, the core should be removed from the cavity and additional filling should be injected into the cavity and the core re-inserted. Preferably, additional injection of filling and reinsertion of the core should be repeated until there is no foreign matter or air bubbles in the filling.

The diffusing tip can be allowed to cure in air. After curing, filling that seeped from the hole should be removed by pulling three to four millimeters of filling out of the hole and then cut. The elastic property of the filling can then pull the filling back into the hole.

An epoxy, such as a 2-part Optical epoxy, is mixed with a hardener in a 3:1 ratio and is transferred to an injector barrel supplied with a blunt ended needle (e.g., a 27 gauge needle) and allowed to thicken. The remaining epoxy mix is deposited into the hole drilled through the outer housing and is applied to the barrier between the outer housing and the buffer of the light guide. When the epoxy mix cures, the filled areas are smoothed to ensure the hole and barrier are flush with the rest of the outer housing.

The manufacturing processes described above are exemplary, and various alternative techniques can be practiced to construct the diffusing tip assemblies. For example, automated extrusion methods or injection molding approaches can be employed to mass produce fibers with integral diffusive tip assemblies.

Although the present invention has been described in terms of various embodiments, it is to be understood that such disclosure is not intended to be limiting. Various alterations and modifications will be readily apparent to those of skill in the art. Accordingly, it is intended that the appended claims be interpreted as covering all alterations and modifications as fall within the spirit and scope of the invention.

The invention claimed is:

1. A light diffusing tip comprising:
   an outer housing having a length, a proximal end, a distal end, and defining a cavity extending the length from the proximal end to the distal end; a cavity axis extending the length through a first portion and a second portion of the cavity;
   a light guide with a distal end being located within the first portion of the cavity;
   an insert having an outer surface and a base, an apex of the outer surface having a cross-section that is smaller than a cross-section of the base;
   the insert being located within the second portion of the cavity;
   a coating covering the outer surface of the insert;
   a filling deposited within the cavity between the distal end of the light guide and the outer surface of the insert; and,
   wherein at least a portion of light directed into the proximal end is diffused by the filling, the coating, and the outer surface through the outer housing in radial directions generally transverse the cavity axis, and through the base; and wherein a hole through the distal end of the outer housing is sealed with the filling.

2. The light diffusing tip of claim 1, wherein the filling has a first concentration of light scattering particles and the coating has a second concentration of light scattering particles.

3. The light diffusing tip of claim 2, wherein the first concentration of light scattering particles is less than the second concentration of light scattering particles.

4. The light diffusing tip of claim 2, wherein the first concentration of light scattering particles is between 0.0025% and 0.0050%.

5. The light diffusing tip of claim 2, wherein the second concentration of light scattering particles is between 0.15% and 0.30%.

6. The light diffusing tip of claim 2, wherein all the light scattering particles have lengths less than 18 nm.

7. The light diffusing tip of claim 1, wherein the insert is comprised of at least one of glass, silica, silicon, silicone, quartz, plastic, polymer or fluoropolymer, sapphire, plastic, engineered plastic, or metal.

8. The light diffusing tip of claim 1, wherein the filling and the coating are comprised of at least one of silica, silicon, silicone, glass, plastic, polymer, optical epoxy, UV curable epoxy, titanium oxide, titanium dioxide, alumina oxide, aluminum oxide, powdered diamond, diamond dust, zinc oxide, silver, gold, zirconium oxide, cubic zirconia, zirconia nanoparticles, or a combination of any one of these.

9. The light diffusing tip of claim 1, wherein the diffused light creates a radiance pattern that is within 90% uniformity.

10. The light diffusing tip of claim 1, wherein at least 90 percent of the outer surface of the insert is covered with the coating.

11. The light diffusing tip of claim 1, wherein at least 90 percent the outer surface of the insert is smooth, abraded, or etched.

12. The light diffusing tip of claim 1, wherein at least 90 percent of the base of the insert is smooth, abraded, or etched.

13. The light diffusing tip of claim 1, wherein the length of the outer housing is between 5 mm and 50 mm.

14. The light diffusing tip of claim 1, wherein the insert is conical.

15. The light diffusing tip of claim 1, wherein the insert has a length of between 2.5 mm and 45 mm.

16. The light diffusing tip of claim 1, wherein the insert is fused, bonded, or mechanically fixed to the outer housing.

17. The light diffusing tip of claim 16, wherein the distal end of the outer housing is sealed with a shaped cap having a distal contour that is hemispherical, conical, beveled, or flat.

18. The light diffusing tip of claim 17, wherein the shaped cap comprises a light blocking, light reflecting, or light absorbing material.

19. The light diffusing tip of claim 1, wherein the filling, the coating, and the insert fill more than 90 percent of the cavity so as to displace a gas in the cavity.

20. The light diffusing tip of claim 1, wherein the insert is centered about the cavity axis.

21. The light diffusing tip of claim 1, wherein the insert is offset from the cavity axis.

22. The light diffusing tip of claim 1, wherein light diffused through the base is reflected towards the proximal end by a reflecting element adjacent the base.

23. The light diffusing tip of claim 1, wherein light diffused through the base is absorbed by a light blocking element adjacent the base.

24. A laser diffusion apparatus comprising:
   a light guide having at least one lower refractive index layer circumferentially disposed about a core, the light guide extending from a proximal end to a distal end; the proximal end being configured to receive light from at least one source, and the distal end having at least one of the lower refractive index layers removed;
   an outer housing having a length and defining a cavity, the cavity having a cavity axis; wherein the cavity axis extends through a first portion and a second portion of the cavity;
   a first light scattering medium having a first concentration of light scattering particles; wherein the first light scattering medium substantially fills the cavity;
   a second light scattering medium having a second concentration of light scattering particles;
   an insert having an outer surface and a base; with the second light scattering medium coating the outer surface, an apex of the outer surface having a cross-section that is smaller than a cross-section of the base;
   wherein the distal end of the light guide is fixed within the first portion of the cavity by an adhesive;
   wherein the insert is fixed within the second portion of the cavity by attaching the base to the outer housing; and,
   wherein a light from the source is emitted by the core and is diffused by the first light scattering medium, the outer surface of the insert, and the second light scattering medium in generally radial directions transverse the cavity axis and through the base; and wherein an energy density measured across the base is the same as an energy density measured along the length of the outer housing.

25. The laser diffusion apparatus of claim 24, wherein the light is diffused within 90 percent uniformity.

26. The laser diffusion apparatus of claim 24, wherein the insert is conical.

27. The laser diffusion apparatus of claim 24, wherein the first concentration of light scattering particles is less than the second concentration of light scattering particles.

28. The laser diffusion apparatus of claim 24, wherein the first and second light scattering mediums and the insert are comprised of at least one of silica, silicon, silicone, glass, plastic, polymer, optical epoxy, UV curable epoxy, titanium oxide, titanium dioxide, alumina oxide, aluminum oxide, powdered diamond, diamond dust, zinc oxide, silver, gold, zirconium oxide, cubic zirconia, zirconia nanoparticles or a combination of any one of these.

29. The laser diffusion apparatus of claim 24, wherein substantially all of the outer surface is smooth, abraded, or etched.

30. The laser diffusion apparatus of claim 24, wherein the second light scattering medium coating the outer surface of the insert contacts the core.

31. A method of making a light diffusing tip comprising:
forming a length of an outer housing, the outer housing having a proximal end, a distal end, and defining a cavity extending the length of the outer housing from the proximal end to the distal end;
forming a hole through a wall of the outer housing adjacent the distal end;
forming an insert; the insert having an outer surface and a base;
mixing a filling having a first concentration of light scattering particles;
mixing a coating having a second concentration of light scattering particles;
covering the outer surface of the insert with the coating;
placing the insert into the cavity at the distal end;
depositing the filling into the cavity at the proximal end until the filling is discharged from the hole;
inserting an exposed core of a light guide into the cavity at the proximal end; and,
removing any of the filling that has been discharged from the hole.

32. The method of making a light diffusing tip of claim 31, further comprising abrading or etching the outer surface of the insert.

33. The method of making a light diffusing tip of claim 31, further comprising attaching the base of the insert to the distal end of the outer housing.

34. The method of making a light diffusing tip of claim 31, further comprising removing gas from the filling with centrifugal force.

35. The method of making a light diffusing tip of claim 31, further comprising centering the insert on a cavity axis.

36. The method of making a light diffusing tip of claim 31, further comprising attaching the proximal end of the light diffusing tip to a light guide.

37. A light diffusing tip comprising:
a capillary tube having a capillary tube refractive index, the capillary tube having a proximal end, a distal end, and defining a cavity extending from the proximal end to the distal end; a cavity axis extending through a first portion and a second portion of the cavity; a hole through the capillary tube at the distal end of the second portion of the cavity;
the capillary tube forming a housing to contain an insert, a coating, and a filling;
the insert having an insert refractive index, the insert comprising an outer surface and a base; the insert being fixed within the second portion such that a portion of the outer surface contacts the capillary tube distal the hole;
the coating having a coating refractive index; the coating covering a portion of the outer surface of the insert;
the filling having a filling refractive index; the filling is inserted into the first portion and the second portion of the cavity and through the hole;
wherein at least a portion of light directed into the capillary tube at the proximal end is scattered by the filling, the coating, and the insert in generally radial directions transverse the cavity axis and through the base; and,
wherein the scattered light creates a radiance pattern of substantially uniform intensity along the length and across the base.

38. The light diffusing tip of claim 37, wherein the coating refractive index is greater than the filling refractive index.

39. The light diffusing tip of claim 37, wherein the filling refractive index is greater than the insert refractive index.

40. The light diffusing tip of claim 37, wherein the insert refractive index is less than both the coating refractive index and the filling refractive index.

* * * * *